United States Patent [19]

Schul et al.

[11] Patent Number: 5,047,223

[45] Date of Patent: Sep. 10, 1991

[54] SEPARATION OF PHOSPHORIC ACID FROM AQUEOUS SOLUTIONS OF THIAMINE PHOSPHATES

[75] Inventors: Wolfgang Schul, Ludwigshafen; Joachim Paust, Neuhofen, both of Fed. Rep. of Germany

[73] Assignee: BASF Aktiengesellschaft, Ludwigshafen, Fed. Rep. of Germany

[21] Appl. No.: 477,476

[22] Filed: Feb. 9, 1990

[30] Foreign Application Priority Data

Mar. 2, 1989 [DE] Fed. Rep. of Germany ....... 3906633

[51] Int. Cl.$^5$ .................. C01B 25/16; C07D 239/02; C07D 415/00
[52] U.S. Cl. .......................... 423/321 S; 423/321 R; 544/327
[58] Field of Search .................. 423/321 S, 321 R; 544/327

[56] References Cited

U.S. PATENT DOCUMENTS 3,361,527  1/1968  Hinkebein et al. ............ 423/321 S
3,367,749  2/1968  Koerner et al. ............... 423/321 R

FOREIGN PATENT DOCUMENTS 0049429  4/1982  European Pat. Off. .
1085527  7/1960  Fed. Rep. of Germany .

OTHER PUBLICATIONS

Verlag Chemie, Weinheim, New York, 1979, pp. 242–245, C. Reichardt, "Solvent Effects in Organic Chemistry".

*Primary Examiner*—Gregory A. Heller
*Attorney, Agent, or Firm*—Oblon, Spivak, McClelland, Maier & Neustadt

[57] ABSTRACT

Phosphoric acid is separated from aqueous solutions of thiamine phosphates which are obtained in the phosphorylation of thiamine, with or without subsequent partial hydrolysis, by a process in which the phosphoric acid is converted with a virtually water-insoluble or only slightly water-soluble tertiary amine into the corresponding salt and the latter is extracted with a virtually water-immiscible or only slightly water-miscible solvent of moderate polarity. In a particularly advantageous procedure, the phosphoric acid is extracted with a mixture of a virtually water-insoluble or only slightly water-soluble tertiary amine and a virtually water-immiscible or only slightly water-miscible solvent of moderate polarity.

5 Claims, No Drawings

SEPARATION OF PHOSPHORIC ACID FROM AQUEOUS SOLUTIONS OF THIAMINE PHOSPHATES

Cocarboxylase (also referred to as thiamine pyrophosphate or thiamine diphosphate) of the formula I is a prosthetic group and, together with specific proteins, forms several enzymes which catalyze a number of important reactions in the metabolism of the human and animal organism.

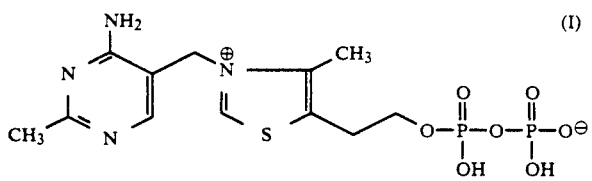

Under certain conditions, for example where there is enzyme insufficiency or oxygen deficiency in the tissue, the mechanism of phosphorylation of vitamin B1 to cocarboxylase may be disturbed. In such cases, therapy with cocarboxylase is of just as much interest as in diabetic acidosis, certain forms of peripheral vascular disorders, neuralgia or herpes zoster.

Since the isolation of the coenzyme of cocarboxylase from yeast in 1937, there has been no lack of attempts to develop an advantageous process for the preparation thereof. A summary of known processes appears in the description of DE-A-10 85 527. All industrially relevant syntheses of cocarboxylase which have been described start from thiamine, which is reacted with a very wide range of phosphorylating agents. The most freuqently used phosphorylating agent is highly concentrated phosphoric acid. As described in DE-A-10 85 527, highly concentrated orthophosphoric acid contains only about 25% of pyrophosphoric acid, so that cocarboxylase can in theory be formed in a yield of not more than 25%. The yield can only be increased by partially hydrolyzing one of the higher thiamine polyphosphates formed as a byproduct, without simultaneously degrading the cocarboxylase itself.

The principal difficulty in the preparation of cocarboxylase is therefore in isolating the cocarboxylase in a very advantageous manner from the mixture of phosphoric acid and the various thiamine phosphates, which mixture is obtained in the phosphorylation of thiamine. Because of the sensitivity of the thiamine phosphates to acid, it has proven advantageous for this purpose to separate off the excess phosphoric acid as far as possible before the actual isolation of the esters.

In the prior art, the phosphoric acid is generally separated off by repeated precipitation of the thiamine phosphates with solvents, such as methanol or acetone, and separation of the said phosphates from the aqueous solution containing phosphoric acid. The amounts of solvents required for this purpose are considerable. Moreover, complete removal of the phosphoric acid is not possible by this procedure.

Another possible method is the treatment of the phosphoric acid-containing thiamine phosphate solutions with basic ion exchangers. The disadvantage here is that very large amounts of ion exchangers are required and that the thiamine phosphates are obtained in highly dilute solution as a result of the treatment with ion exchangers.

We have found that the excess phosphoric acid can be completely separated off by liquid-liquid extraction of the thiamine phosphate solutions obtained in the phosphorylation of thiamine, with a mixture of a suitable water-insoluble tertiary amine and a water-immiscible solvent of moderate polarity. In this procedure, the phosphoric acid is converted with the water-insoluble amine into the corresponding salt, which is then extracted by the water-immiscible solvent. It was very surprising that, in this extraction of the phosphoric acid, the thiamine phosphates, which are also capable of salt formation with amines, are not extracted but remain virtually quantitatively in the aqueous solution.

The present invention therefore relates to a process for the separation of phosphoric acid from aqueous solutions of thiamine phosphates which are obtained, for example, in the preparation of cocarboxylase by phosphorylation of thiamine, with or without subsequent partial hydrolysis, wherein the phosphoric acid is converted with a virtually water-insoluble or only slightly water-soluble tertiary amine into the corresponding salt, and the latter is extracted with a virtually water-immiscible or only slightly water-miscible solvent of moderate polarity.

The novel process is particularly advantageously carried out by a method in which the phosphoric acid is extracted with a mixture of a virtually water-insoluble or only slightly water-soluble tertiary amine and a virtually water-immiscible or only slightly water-miscible solvent of moderate polarity.

The extracting agent can be regenerated by simple back-extraction with aqueous alkaline solutions (eg. NaOH or KOH). After the extraction, the thiamine phosphates are present in the aqueous phase and can be separated in a conventional manner by ion exchange chromatography.

Since the excess phosphoric acid can be virtually completely removed by the extraction, substantially smaller amounts of ion exchangers are required here.

Observations to date have shown that suitable tertiary amines for the novel process are in principle all tertiary amines which have little or no water solubility, so that, provided that they cannot react in other ways with the reactants owing to functional groups, their chemical nature is unimportant. Examples are aliphatic tertiary amines of, in total, 8 to 40, preferably 12 to 36, carbon atoms, especially trioctylamine, trihexylamine and tridodecylamine, aliphatic-cycloaliphatic tertiary amines, such as N,N-dimethylcyclohexylamine and aliphatic-araliphatic tertiary amines, such as N,N-dimethylbenzylamine.

The readily obtainable and therefore cheap amines trioctylamine and tridodecylamine are particularly advantageously used.

The tertiary amines are generally used in the amounts required for salt formation. In a particularly advantageous procedure, salt formation is effected directly in the presence of the virtually water-immiscible solvent of moderate polarity which is used for the extraction. In practice, this means that the phosphoric acid is extracted with a mixture of the water-insoluble or only slightly water-soluble amine and the water-immiscible or only slightly water-miscible solvent. Mixtures which contain the amine in amounts of from 10 to 80, preferably from 40 to 70, % by weight, based on the solvent, are used for this purpose. If mixtures which contain only small amounts of amine are used, either large amounts of the amine/solvent mixture must be used or the extraction process must be repeated several times. If an amine/solvent mixture which contains large amounts of amine is employed, a single extraction process may be sufficient.

Suitable water-immiscible or only slightly water-miscible solvents of moderate polarity are essentially those solvents which have an $E_T$ value of about 50 to about 30 kcal/mol (from 211 to 125 kJ/mol) (cf. Chr. Reichardt, Solvent Effects in Organic Chemistry, Verlag Chemie, 1979, especially pages 242–245). Examples are alcohols of 4 to 8 carbon atoms, ethers, such as diethyl ether, methyl tert-butyl ether, diphenyl ether or di-n-butyl ether, and ketones of 5 to 8 carbon atoms, such as diethyl ketone, methyl isobutyl ketone, acetophenone or cyclohexanone, and hydrocarbons, such as toluene. Ethyl acetate and halohydrocarbons can in principle also be used but are not very advantageous for reasons relating to process engineering.

Methylisobutylcarbinol, 3-ethylpentanol, 1-hexanol, methylcyclohexanol, methyl isobutyl ketone and methyl tert-butyl ether are particularly advantageously used.

The solvents are used in general in amounts of from 1 to 4, preferably from 1.5 to 2, kg per kg of the phosphoric acid to be extracted. In the mixture with the tertiary amine, it is present in amounts of from 20 to 90, preferably from 30 to 60, % by weight, based on the tertiary amine.

If the mixture of tertiary amine and the solvent is not used, ie. if the tertiary amine is added to the phosphoric acid-containing aqueous solution of thiamine phosphates in the absence of the water-immiscible solvent, the resulting salt may be obtained in greasy form and may therefore present difficulties in the subsequent extraction.

The extraction of the phosphoric acid is complete when the aqueous solution has a pH of from 3 to 4, in particular from 3.2 to 3.4.

The novel process is suitable for separating phosphoric acid from phosphoric acid-containing aqueous solutions of thiamine phosphates which are obtained in the phosphorylation of thiamine.

The composition of the mixture of thiamine phosphates which is obtained in the phosphorylation of thiamine is dependent on the amount of thiamine introduced into the phosphoric acid. At low thiamine/phosphoric acid ratios, virtually 50% of higher thiamine phosphates are formed, whereas the content of thiamine monophosphate increases to above 60% at high thiamine/phosphoric acid ratios.

The thiamine phosphates are hydrolyzed in acidic solution. The diphosphates, triphosphates and higher phosphates are much more unstable to aqueous acids than thiamine monophosphate. At a pH of less than 1, which is reached when the crude phosphorylation product is dissolved in water, the rate of hydrolysis of the higher phosphates is relatively high.

If the crude phosphorylation product has a high content of higher thiamine phosphates, it is advisable first to subject the mixture obtained in the phosphorylation to partial hydrolysis. For this purpose, the crude thiamine phosphate obtained in the phosphorylation is generally heated in water at a pH of from 0.5 to 3, preferably from 0.5 to 1.5, to 30–100° C., preferably 50–80° C. The most advantageous conditions can be determined in each case by investigating the mixture by HPLC. The longer the crude thiamine phosphate is heated in water, the greater will be the content of thiamine monophosphate. By prolonged partial hydrolysis, ie. by heating the crude thiamine phosphate mixture in water for about 2–3 hours, it is possible, if desired, to obtain aqueous phosphoric acid-containing solutions which contain predominantly thiamine monophosphate and from which the thiamine monophosphate likewise required can be obtained in a simple manner after the removal, according to the invention, of the phosphoric acid.

After the extraction of the excess phosphoric acid, the thiamine phosphates can be isolated in a conventional manner.

Cocarboxylase and thiamine monophosphate are advantageously isolated by a method in which a major part of the thiamine monophosphate is precipitated as crystalline thiamine phosphate from the thiamine phosphate solutioin, freed from phosphoric acid by extraction, by the addition of a lower alcohol or acetone, and carboxylase is obtained from the remaining solution having a higher cocarboxylase content in a conventional manner by ion exchange chromatography, after the organic solvent has been distilled off.

The isolation of the thiamine phosphates is described in more detail in, for example, the abovementioned DE-A-10 85 527.

Any desired salts of the cocarboxylase can also be prepared in a conventional manner from the cocarboxylase tetrahydrate obtained in the isolation step.

With the aid of the novel process, cocarboxylase can be isolated in a simpler and more advantageous manner from the mixtures of orthophosphoric acid and various thiamine phosphates, which mixtures are obtained in the phosphorylation of thiamine.

Another advantage of the thiamine phosphate solution obtained by complete removal of phosphoric acid by extraction is that a major part of the thiamine monophosphate can be obtained directly as crystalline thiamine monophosphate (saleable commercial product) by the addition of an organic solvent, such as methanol, ethanol or acetone. The remaining solution having a higher cocarboxylase content can be purified in a conventional manner by ion exchange chromatography after the organic solvent has been distilled off. Owing to the lower thiamine monophosphate content of this solution, substantially smaller amounts of ion exchangers are required.

By prolonged partial hydrolysis of the solution, obtained by phosphorylation of thiamine, of thiamine phosphates, subsequent extraction of the phosphoric acid and addition of an organic solvent, such as methanol, ethanol or acetone, virtually the entire content of thiamine phosphates can be isolated in a simple manner in the form of crystalline, saleable thiamine monophosphate.

The Examples which follow illustrate the novel process.

The Examples are preceded by some explanations of the analysis used for the thiamine phosphates.

The analysis of the thiamine phosphorylation products was carried out by HPLC on a reverse phase silica gel column (cf. M. Kumura et al., J. Chromatography, 332 (1985), 181–188).

Column: RP 18.7 μm, 250×8 mm

Mobile phase: 997 ml of 0.2 M $NaH_2PO_4$ buffer in $H_2O$
  3 ml of acetonitrile Pressure: 115 bar For the detection of thiamine and the phosphorylation products, measurements were made with a UV detector at λ=235 nm, and phosphoric acid was detected by means of a downstream RI detector.

The phosphorylation product ratios were determined from the UV integrator printout and did not correspond to the molar yields of the various phosphorylation reaction products. These can be obtained by incorporating the various extinction coefficients of the individual phosphate species, but this is not necessary for relative comparisons of the phosphorylation reactions.

EXAMPLE 1

A) Phosphorylation of thiamine chloride hydrochloride 200 g (0.59 mol) of thiamine chloride hydrochloride were stirred with 250 g of orthophosphoric acid for 1 hour (h) at 100° C. The mixture was heated to 120° C., after which 200 g of phosphorus pentoxide were added, so that the evolution of HCl gas which occurred remained under control. After reaction for a further 15 minutes, the reaction mixture was allowed to cool. 544 g of a phosphoric acid-containing thiamine phosphate mixture were obtained, the said mixture having the following composition according to HPLC:
33.7% of cocarboxylase,
37.2% of thiamine monophosphate,
15.0% of thiamine triphosphate and
13.1% of thiamine tetraphosphate.

B) Partial hydrolysis of the thiamine phosphate mixture

The crude phosphate (544 g) which had solidified to a glassy material was dissolved in 1,088 ml of water and the solution was then heated at 70° C. for 1 h and then investigated by HPLC. It had the following composition:
61.4% of thiamine monophosphate,
31.5% of cocarboxylase and
2.6% of thiamine triphosphate.

C) Extraction of the phosphoric acid

The solution was cooled and then extracted with twice 1 l of a mixture of methylisobutylcarbinol containing 75% by weight of tri-n-octylamine (extracting agent can be recycled) in order to remove the principal amount of free phosphoric acid. 907 g of a crude phosphate solution (pH 3.3) were obtained, the said solution having the following composition:
66.9% of thiamine monophosphate,
30.2% of cocarboxylase and
1.5% of thiamine triphosphate.

D) Separation of the thiamine phosphates by means of ion exchangers

The thiamine phosphate solution (907 g) obtained after extraction of the crude phosphate was separated over 2 ion exchange columns. The columns contained:
1) 400 ml of Amberlite, IRA 93 (weakly basic, OH form)
2) 3,000 ml of Lewatit IR-120 (strongly acidic, H+form).

The solution emerging from the weakly basic ion exchanger (IRA 93) was fed directly to the acidic ion exchanger Lewatit IR-120. After a first fraction of 300 ml, 1.2 l of a cocarboxylase solution having the following composition were obtained:
99.5% of cocarboxylase and
0.5% of thiamine monophosphate.

After the cocarboxylase solution (1.2 l) had been evaporated down to about 100 ml under about 40 mbar and 400 ml of methanol had been added, 54 g (18%, based on thiamine.HCl used) of cocarboxylase tetrahydrate were obtained.

E) Regeneration of the ion exchangers and isolation of thiamine orthophosphoric acid bishydrochloride a) The weakly basic ion exchanger (Amberlite IRA 93) was regenerated with 1.0 l of a 1.5% strength aqueous NaOH solution and, after being washed neutral with 3 l of H₂O, could be used for further separation.

b) The acidic ion exchanger IR-120 was regenerated with 5 l of a 10% strength aqueous HCl solution and, after being washed neutral with 20 l of H₂O, could be used for further separations. The regeneration solution (5 l) containing hydrochloric acid was evaporated down to 400 ml (under about 40 mbar).

The addition of 2 l of MeOH gave 153 g (57%, based on thiamine hydrochloride used) of thiamine orthophosphoric acid bishydrochloride, which can be used instead of thiamine chloride hydrochloride for further phosphorylations.

Phosphoric acid was removed virtually quantitatively by extraction in a similar manner from aqueous solutions of thiamine phosphates which had been prepared by phosphorylation of thiamine, with or without subsequent partial hydrolysis:
a) by extraction 3 times with a mixture consisting of 40% by weight of tri-n-dodecylamine and 60% by weight of methyl tert-butyl ether;
b) by extraction twice with a mixture consisting of 50% by weight of tri-n-octylamine and 50% by weight of 1-hexanol;
c) by extraction 3 times with a mixture consisting of 60% by weight of tri-n-hexylamine and 40% by weight of 3-ethylpentanol and
d) by extraction 3 times with a mixture consisting of 40% by weight of tri-n-butylamine and 60% by weight of methyl isobutyl ketone.

EXAMPLE 2

200 g of thiamine chloride hydrochloride were phosphorylated with 250 g of orthophosphoric acid similarly to Example 1A, the resulting thiamine phosphate mixture was partially hydrolyzed similarly to Example 1B and the resulting solution was extracted, similarly to Example 1C, with twice 1 l of a mixture of methyl isobutylcarbinol and 75% by weight of tri-n-octylamine.

1,100 ml of the extracted solution contained 318 g of dry substance having the following composition:
72.7% of thiamine monophosphate,
23.4% of cocarboxylase and
1.0% of thiamine triphosphate.

1,100 ml of ethanol were added to the 1,100 ml of the extracted crude phosphate solution at 50° C. and the resulting mixture was cooled to room temperature in the course of 1 h. It was then left to stand for about a further 30 min at room temperature, after which the precipitated crystals were filtered off.

The crystals (180 g of dry substance) contained:
98.0% of thiamine monophosphate and 1.5% of cocarboxylase.

The crystals were dried at 40° C. under reduced pressure. They can then be used as such or recycled to the phosphorylation reaction.

The mother liquor (137 g of dry substance) contained:
35.8% of thiamine monophosphate,
53.5% of cocarboxylase and 2.3% of thiamine triphosphate.

The mother liquor was distilled under reduced pressure at from 30° to 40° C. to separate off the ethanol. The residue obtained was purified by ion exchange chromatography over 350 ml of Amberlite IRA 93 (weakly basic; OH form) and Lewatit IR-120 in a known manner.

1,000 ml of a cocarboxylase-containing solution were obtained, the said solution giving 54 g of cocarboxylase tetrahydrate after evaporation and crystallization.

EXAMPLE 3

200 g of thiamine chloride hydrochloride were phosphorylated with a mixture of 250 g of orthophosphoric acid and 200 g of $P_2O_5$ similarly to Example 1A, the resulting thiamine phosphate mixture was partially hydrolyzed by heating at 70° C. for 3½ hours and the solution obtained was extracted, similarly to Example 1C, with twice 1 l of a mixture of methylisobutylcarbinol and 75% by weight of tri-n-octylamine.

1,100 ml of the extracted solution contained 318 g of dry substance having the following composition: 94% of thiamine monophosphate and 3% of cocarboxylase.

1,100 ml of ethanol were added to the 1,100 ml of the extracted crude phosphate solution at 50° C. and the resulting mixture was cooled to room temperature in the course of 1 h. It was then left to stand for about 30 minutes at room temperature and the precipitated crystals were then filtered off.

The crystals (240 g of dry substance) contained: 99.6% of thiamine monophosphate.

The crystals were dried at 40° C. under reduced pressure. They can be used as such.

We claim:

1. A process for separating phosphoric acid from aqueous solutions of thiamine phosphates which are obtained in the phosphorylation of thiamine, with or without subsequent partial hydrolysis, wherein the phosphoric acid is converted with a virtually water-insoluble or only slightly water-soluble tertiary amine selected from the group consisting of an aliphatic or aliphatic-cycloaliphatic tertiary amine of 8 to 40 carbon atoms and an aliphatic-araliphatic tertiary amine of 9 to 36 carbon atoms into the corresponding salt and the latter is extracted with a virtually water-immiscible or only slightly water-miscible solvent of moderate polarity selected from the group consistin of an aliphatic or cycloaliphatic alcohol of 4 to 8 carbon atoms, an ether of 4 to 12 carbon atoms, a ketone of 5 to 8 carbons atoms and a hydrocarbon of 6 to 10 carbon atoms.

2. A process as claimed in claim 1, wherein the phosphoric acid is extracted with a mixture of a virtually water-insoluble or only slightly water-soluble tertiary amine and a virtually water-immiscible or only slightly water-miscible solvent of moderate polarity.

3. A process as claimed in claim 1, wherein the virtually water-insoluble or only slightly water-soluble tertiary amine used is trioctylamine or tridodecylamine.

4. A process as claimed in claim 1, wherein the virtually water-immiscible or only slightly water-miscible solvent of moderate polarity which is used is methylisobutylcarbinol, 3-ethylpentanol, 1-hexanol, methylcyclohexanol, methyl isobutyl ketone or methyl tert-butyl ether.

5. In a process for the production of cocarboxylase (thiamine pyrophosphate) and/or thiaminemonophosphate by phosphorylation of thiamine with highly concentrated orthophosphoric acid, with or without subsequent partial hydrolysis, subsequent separation of the excess phosphoric acid from the mixture of excess phosphoric acid and the thiamine phosphates obtained and subsequent actual isolation of the thiaminphosphates, the improvement which comprises that the separation of excess phosphoric acid from said mixture is carried out by converting the phosphoric acid with a virtually water-insoluble or only slightly water-soluble tertiary amine selected from the group consisting of an aliphatic or aliphatic-cycloaliphatic tertiary amine of 8 to 40 carbon atoms, and an aliphatic-araliphatic tertiary amine of 9 to 36 carbon atoms into the corresponding salt and extracting the latter with a virtually water-immiscible or only slightly water-miscible solvent of moderate polarity selected from the group consisting of an aliphatic or cycloaliphatic alcohol of 4 to 8 carbon atoms, an ether of 4 to 12 carbon atoms, an ether of 4 to 12 carbon atoms, a ketone of 5 to 8 carbon atoms and a hydrocarbon of 6 to 10 carbon atoms.

* * * * *